United States Patent
Kuo et al.

(10) Patent No.: US 7,355,048 B2
(45) Date of Patent: *Apr. 8, 2008

(54) PROCESS FOR PREPARING 1-(6-METHYLPYRIDIN-3-YL)-2-[4-(METHYLSULPHONYL)PHENYL]ETHANONE

(75) Inventors: David Kuo, Radnor, PA (US); James E. Leresche, Visp (CH); Ralf Proplesch, Eyholz (CH); Jean-Paul Roduit, Grone (CH); Yves Bessard, Sierre (CH); Erich Armbruster, Naters (CH)

(73) Assignees: Lonza Ltd., Basel (CH); Merck & Co. Inc., Rahway, NJ (US)

( * ) Notice: Subject to any disclaimer, the term of this patent is extended or adjusted under 35 U.S.C. 154(b) by 452 days.

This patent is subject to a terminal disclaimer.

(21) Appl. No.: 11/029,489

(22) Filed: Jan. 6, 2005

(65) Prior Publication Data

US 2005/0159458 A1    Jul. 21, 2005

Related U.S. Application Data

(62) Division of application No. 09/868,941, filed as application No. PCT/EP00/00240 on Jan. 13, 2000, now Pat. No. 7,141,673.

(60) Provisional application No. 60/145,996, filed on Jul. 29, 1999.

(30) Foreign Application Priority Data

Jan. 14, 1999    (EP) .................... 99100590

(51) Int. Cl.
*C07D 211/70* (2006.01)
*C07D 211/82* (2006.01)
*C07D 211/90* (2006.01)

(52) U.S. Cl. .................. 546/286; 546/315; 546/344

(58) Field of Classification Search ............ 546/315, 546/286, 344

See application file for complete search history.

(56) References Cited

U.S. PATENT DOCUMENTS

| 3,313,683 | A  | 4/1967  | Taylon         |
| 4,155,909 | A  | 5/1979  | Sanders et al. |
| 5,596,008 | A  | 1/1997  | Lee            |
| 6,600,046 | B2 | 7/2003  | Bessard et al. |
| 6,642,387 | B2 | 11/2003 | Amano et al.   |

FOREIGN PATENT DOCUMENTS

| FR | 2074674  | 8/1971  |
| WO | 98/03484 | 1/1998  |
| WO | 98/47871 | 10/1998 |
| WO | 99/15503 | 4/1999  |
| WO | 99/55830 | 11/1999 |

OTHER PUBLICATIONS

Friesen et al., Bioorg. & Med. Chem. Letters, 8, (1998), 2777-2782.
Mizzoni, (Klingsberg, Editor), Pyridineand its Derivatives, Part chp. IV, XIV, (1964), 123-141.
March, Advanced Organic Chemistry, 4th edition, 893-895.

*Primary Examiner*—Janet L. Andres
*Assistant Examiner*—Raymond Covington
(74) *Attorney, Agent, or Firm*—Fisher, Christen & Sabol

(57) ABSTRACT

A four-step process for preparing 1-(6-methylpyridin-3-yl)-2-[4-(methylsulfonyl)phenyl]ethanone of the formula:

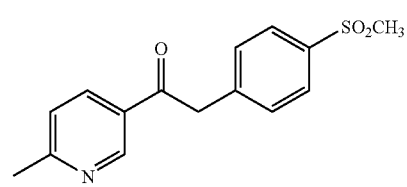

starting from 2-methyl-5-ethylpyridine. 1-(6-Methylpyridin-3yl)-2-[4-(methylsulfonyl)phenyl]ethanone is an intermediate for preparing inhibitors.

12 Claims, No Drawings

PROCESS FOR PREPARING 1-(6-METHYLPYRIDIN-3-YL)-2-[4-(METHYLSULPHONYL)PHENYL]ETHANONE

This is a divisional application of U.S. patent application Ser. No. 09/868,941, filed on Nov. 4, 2003, and that has a 371(c) date of Nov. 4, 2003, now U.S. Pat. No. 7,141,673, that is a 371 National Stage Application of International Patent Application PCT/EP00/00240, filed on Jan. 13, 2000, that has priority benefit of European Patent Application 99100590.1, filed on Jan. 14, 1999, and that has benefit of Provisional Application Ser. No. 60/145,996, filed on Jul. 29, 1999, that has priority benefit of European Patent Application 9910059.1, filed on Jan. 14, 1999.

Description

The invention comprises a novel process for preparing 1-(6-methylpyridin-3-yl)-2-[(4-(methyl-sulphonyl)phenyl] ethanone of the formula

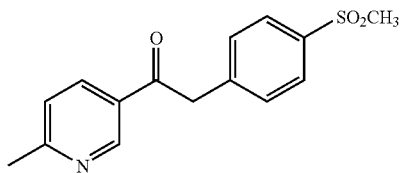

I 1-(6-methylpyridin-3-yl)-2-[(4-(methylsulphonyl)-phenyl] ethanone is an important intermediate for preparing so-called COX-2 inhibitors, pharmaceutically active compounds having analgesic and anti-inflammatory action (R. S. Friesen et al., Bioorganic & Medicinal Chemistry Letters 8 (1998) 2777-2782; WO 98/03484). 1-(6-methylpyridin-3-yl)-2-[(4-(methylsulphonyl)-phenyl]ethanone of the formula I is a novel compound which is not known from the literature.

It was the object of the invention to provide a novel intermediate for the production of COX-2-inhibitors and to provide an industrially feasible process for preparing the novel intermediate of the formula I.

The object was achieved by the novel process and compound of the invention.

The process according to the invention is characterized by four steps, where in the first step a) 2-methyl-5-ethylpyridine is converted at from 500° C. to 700° C. in the presence of a catalyst into 2-methyl-5-vinylpyridine, in the second step b) the 2-methyl-5-vinylpyridine is converted with ozone and subsequent reductive work-up into 2-methylpyridine-5-carbaldehyde, in the third step c) the 2-methylpyridine-5-carbaldehyde is converted with a dialkylamine and a CN compound into the corresponding N,N-dialkylamino-(6-methyl-3-pyridyl)acetonitrile and finally in the last step d) the N,N,-dialkylamino-(6-methyl-3-pyridyl)acetonitrile is reacted in the presence of a base with a 4-(methylsulphonyl)benzyl halide to give 1-(6-methylpyridin-3-yl)-2-[(4-(methylsulphonyl)phenyl]ethanone to give the end product.

A considerable advantage of the process according to the invention consists in the fact that industrially available 2-methyl-5-ethylpyridine can be used as starting material.

Step a:

The dehydration of 2-methyl-5-ethylpyridine to give 2-methyl-5-vinylpyridine is known from the literature (for example A. Nenz et al., Hydrocarbon Processing, 47(11), 1968, 139-144; U.S. Pat. No. 2,769,773).

The reaction proceeds at from 500° C. to 700° C. in the presence of a large number of different catalysts.

In general, catalysts based on silica, silica gel, iron oxide, zinc oxide, chromium oxide, copper chromite, magnesium oxide, potassium oxide, alumina or boron phosphate, alone or as a mixture, if appropriate applied to a support, are employed.

Good results can be obtained inter alia with a zinc oxide catalyst applied to pumice as support.

It is furthermore advantageous for the reaction to dilute the 2-methylpyridine with steam or an inert gas, but preferably with steam.

The 2-methyl-5-vinylpyridine can be purified in a simple manner, for example by removal of the aqueous phase and subsequent steam distillation or vakuum distillation, such that it is suitable for the subsequent step b).

Step b:

The reaction with ozone is advantageously carried out in the presence of a mineral acid at a temperature of from −20° C. to 0° C., preferably at a temperature of from −15° C. to −5° C. Suitable mineral acids are sulphuric acid or phosphoric acid, and in particular sulphuric acid. Suitable reaction media are water and/or a polar solvent. As a polar solvent $C_{1-6}$ alcohols can be used such as methanol, ethanol, propanol, butanol, pentanol or hexanol. Mixtures of a lower alcohol, such as methanol or ethanol, with water have been found to be useful.

The ozone complex which is formed as an intermediate is worked up reductively, preferably with an alkali metal hydrogen sulphite, to obtain the 2-methyl-5-carbaldehyde.

Suitable alkali metal hydrogen sulphites are sodium or potassium hydrogen sulphite. However, it is also possible to choose other known reducing agents, such as, for example, dimethyl sulphide, thiourea or trimethyl phosphite, or hydrogen in the presence of a suitable catalyst.

In the case of the preferred reductive work-up with alkali metal hydrogen sulphite, the reaction is carried out in essentially the same medium as used for the ozonization, generally at a temperature of from −20° C. to 20° C., preferably from −10° C. to 0° C.

Depending on the further work-up steps, the 2-methylpyridine-5-carbaldehyde or an adduct of alkali metal hydrogen sulphite with the 2-methylpyridine-5-carbaldehyde can be formed, namely a 1-hydroxy-(6-methylpyridine-3-yl)methansulfonic acid salt.

If it is desired to isolate the 2-methyl-5-carbaldehyde, it is possible to selectively extract the reaction mixture at a pH of about 4 to 5 with a suitable organic solvent, such as, for example, with ethyl acetate. Alternatively, but preferred, an adduct of alkali metal hydrogen sulphite with the 2-methylpyridine-5-carbaldehyde may be formed initially, which is then cleaved at a pH of about 10 into the 2-methyl-5-carbaldehyde.

Particularly preferably, however, the adduct of alkali metal hydrogen sulphite with the 2-methyl-pyridine-5-carbaldehyde is employed immediately for further reaction in step c). Thus, it is possible to circumvent isolation of the relatively unstable 2-methylpyridine-5-carbaldehyde in an elegant manner.

The adduct of alkali metal hydrogen sulphite with the 2-methylpyridine-5-carbaldehyde is novel and not known from the literature and accordingly also part of the subject-matter of the invention. The adducts have the general formula

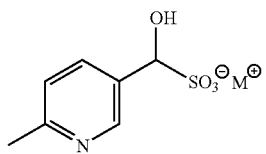

II in which M is an alkali metal, and are referred to as 1-hydroxy-(6-methylpyridin-3-yl)methanesulphonic acid salts. The alkali metal M is advantageously Na or K.

Step c:

The reaction of the 2-methylpyridine-5-carbaldehyde or the adduct of alkali metal hydrogen sulphite with the 2-methylpyridine-5-carbaldehyde is carried out according to the principle of the Strecker synthesis using a CN compound and a dialkylamine to give the corresponding N,N-dialkylamino-(6-methyl-3-pyridyl)acetonitrile.

An aqueous HCN solution or an aqueous solution of an alkali metal cyanide may serve as CN compound here. Particulary suitable dialkylamines are $C_{1-4}$-dialkylamines, wherein $C_{1-4}$ alkyl means methyl, ethyl, n-propyl, iso-propyl, n-butyl, iso-butyl or tertiary-butyl. More preferd dialkylamines are dimethylamine or diethylamine.

The reaction temperature is advantageously in the range of from 0° C. to 30° C.

It may be advantageous to add a water-immiscible solvent, such as, for example, toluene or t-butyl methyl ether. Work-up and isolation of the corresponding N,N-dialkylamino-(6-methyl-3-pyridyl)-acetonitrile can then be carried out by simple phase separation. The N,N-dialkylamino-(6-methyl-3-pyridyl)-acetonitriles of the general formula

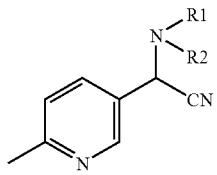

III wherein R1 and R2 are identical or different and are $C_{1-4}$-alkyl, are novel compounds which are not known from the literature, and in consequence form part of the subject-matter of the invention as does the process for their manufacture.

As said above, $C_{1-4}$-alkyl specifically means methyl, ethyl, n-propyl, isopropyl, n-butyl, isobutyl or tert-butyl. The preferred meaning of Alkyl is methyl or ethyl.

Step d:

The conversion of the N,N-dialkylamino-(6-methyl-3-pyridyl)acetonitrile by reaction with the 4-(methylsulphonyl)benzyl halide to give the end product of the formula I is carried out in the presence of a base. A suitable 4-(methylsulphonyl)benzyl halide is 4-(methylsulphonyl)benzyl chloride.

The base used can be an aqueous alkali metal hydroxide solution, preferably an aqueous sodium hydroxide solution, where in this case the presence of a customary phase-transfer catalyst is useful. Suitable phase-transfer catalysts are, for example, tetraalkylammonium halides, such as, for example, tetra-n-butylammonium chloride or tetra-n-butylammonium bromide. The reaction temperature is in the range of from 40° C. to 70° C. It may be advantageous to add a water-immiscible solvent, such as, for example, toluene, methylene chloride or t-butyl methyl ether.

Alternatively and preferably, the base used is an alkali metal alkoxide. Suitable alkali metal alkoxides are, for example, sodium tert-butoxide, potassium tert-butoxide or sodium tert-pentoxide, and preferably potassium tert-butoxide. Recommended solvents are ethers, such as, for example, tetrahydrofuran. The reaction temperature in this variant is generally from 15° C. to 25° C.

The 1-(6-methylpyridin-3-yl)-2-[(4-(methyl-sulphonyl)phenyl]ethanone can be isolated in a manner known to the person skilled in the art, for example by acidifying the reaction mixture, followed by extraction with, for example, toluene. Further purification can be carried out by recrystallization, for example in acetonitrile.

EXAMPLE 1

Preparation of 2-methyl-5-vinylpyridine

Pumice having a particle size of from 6 to 8 mm is moistened with water and mixed with 25% of its dry weight of zinc oxide in powder form, filled moist into the reactor (length of the tube 750 mm, diameter of the tube 60 mm) and left in a stream of nitrogen at from 650° C. to 700° C. for 24 h.

76 ml/h of 2-methyl-5-ethylpyridine together with 87 ml/h of steam were passed over the above-mentioned catalyst at from 670° C. to 680° C. and 665 mbar. At the end of the reactor, a product stream consisting of 40.6% by weight of 2-methyl-5-vinylpyridine and 56.3% of 2-methyl-5-ethylpyridine was taken off. Based on reacted 2-methyl-5-ethylpyridine, a yield of 93.0% was achieved.

To prepare pure 2-methyl-5-vinylpyridine, the product mixture was subsequently subjected to steam distillation (266 mbar, overhead temperature 59° C.-60° C.) or to vakuum distillation (20 mbar, temperature 90° C.).

EXAMPLE 2

Preparation of 2-methylpyridine-5-carbaldehyde 11.92 g of 2-methyl-5-vinylpyridine (content 85%, 85 mmol), 50 ml of methanol and 10 ml of water were initially charged. Concentrated sulphuric acid (9.81 g, 98 mmol) was metered in such that the temperature did not exceed 20° C. The solution was cooled from −12° C. and an ozone/oxygen mixture (about 5% $O_3$ in $O_2$, 50 l/h) was introduced until the 2-methyl-5-vinylpyridine had reacted completely. Water (50 ml) and 40% aqueous $NaHSO_3$ solution (22.7 g, 85 mmol) were carefully metered in. The reaction mixture was warmed to 20° C. and neutralized using 30% NaOH (about 32 g, 0.24 mol). Methanol was distilled off at 30-40° C., and then, to form the bisulphite adduct, another 22.7 g of 40% $NaHSO_3$ solution were added. The mixture was stirred for 30 min, after which the pH was readjusted to neutral, and the neutral impurities were subsequently extracted using 35 ml of t-butyl methyl ether. The aqueous phase was adjusted to pH 10 using 30% NaOH, and 26.5 g of Na$_2$CO$_3$ (0.25 mol) were added. The liberated aldehyde was extracted using 2×80 ml of t-butyl methyl ether. Concentration of the solvent gave 9 g of 2-methylpyridine-5-carbaldehyde as a slightly yellowish oil.

$^1$H-NMR (CDCl$_3$): 2.66 (s, 3H);
7.35 (d, J=8 Hz, 1H);
8.07 (dd, J=8 Hz and 2.1 Hz, 1H);
8.96 (d, J=2.1 Hz, 1H);
10.08 (s, 1H).
$^{13}$C-NMR (CDCl$_3$): 24.98 (CH3);
123.72 (C-5);
129.32 (C-3);
135.88 (C-4);
151.87 (C-2);
164.87 (C-6);
190.51 (C=0).

EXAMPLE 3a

Preparation of N,N-diethylamino-(6-methylpyridin-3-yl)acetonitrile (from 2-methylpyridine-5-carbaldehyde)

At from 10° C. to 15° C., 73.2 g (1.25 eq.) of diethylamine and 100.3 g (1.15 eq.) of a 25% HCN solution were added simultaneously over a period of one hour to a mixture of 98.3 g (1.0 eq.) of 2-methylpyridine-5-carbaldehyde in 200 ml of water and 200 ml of toluene which was stirred efficiently. The reaction mixture was stirred at 300C for 3 h.

The phases were then separated and the aqueous phase was extracted with 2×100 ml of toluene. The organic phases were combined and the toluene was then removed, giving the title product in the form of a yellowish oil and in a yield of 172.3 g (90.1%).

$^1$H-NMR (CDCl$_3$): 8.65 (1H, s);
7.75 (1H, d);
7.20 (1H, d);
5.00 (1H, s);
2.68 (2H, m);
2.59 (13H, s);
2.50 (2H, m);
1.10 (6H, t).
$^1$H-NMR (D$_6$-DMSO): 8.50 (1H, s);
7.70 (1H, d);
7.32 (1H, d);
5.45 (1H, s);
2.58 (2H, m);
2.50 (3H, s);
2.40 (2H, m);
1.02 (6H, t).

EXAMPLE 3b

Preparation of N,N-diethylamino-(6-methylpyridin-3-yl)acetonitrile (Via the Adduct of 2-methylpyridine-5-carbaldehyde with Sodium Hydrogen Sulphite)

The ozonolysis was carried out as in Example 2, starting from 23.84 g of 2-methyl-5-vinylpyridine (83.1% GC, 166.2 mmol). After the impurities had been extracted at neutral pH, the aqueous phase was cooled to 15° C. and diethylamine (21.94 g, 0.3 mol) and then 9.8 g of NaCN (0.2 mol) were added (in each case addition over a period of 10 min). The solution was stirred at 15° C. for 4.5 h, and the product was subsequently extracted with 3×85 ml of toluene. The combined extracts were concentrated. Obtained: 37.4 g of N,N-diethylamino-(6-methylpyridin-3-yl)acetonitrile as an orange oil. Content: 83.7% (GC, % by weight), 0.34% of aldehyde). Yield: 92.7% based on 2-methyl-5-vinylpyridine.

$^1$H-NMR (CDCl$_3$): 1.08 (t, 6H)
2.50 (m, 2H);
2.58 (s, 3H);
2.65 (m, 2H);
5.00 (s, 1H);
7.18 (d, J=8 Hz, 1H);
7.74 (dd, J=8 Hz, 2 Hz, 1H);
8.66 (d, J=2 Hz, 1H).

EXAMPLE 3c

Preparation and Characterization of the Adduct of 2-methylpyridine-5-carbaldehyde with Sodium Hydrogen Sulphite After the addition of bisulphite, the $^1$H- and $^{13}$C-NMR of a sample were measured. The NMR signals of the aldehyde had disappeared completely, and the following signals were observed instead:

$^1$H-NMR (DMSO-d$_6$): 1.96 (s, 3H);
5.01 (s, 1H);
6.85 (d, J=8 Hz, 1H);
7.45 (dd, J=8 and 2 Hz, 1H);
7.93 (d, J=2 Hz, 1H)
$^{13}$C-NMR (DMSO-d$_6$): 20.23 (CH3);
81.78 (CH);
124.14 (C-5);
130.02 (C-3);
138.76 (C-4);
143.08 (C-2);
156.04 (C-6).

EXAMPLE 4a

Preparation of 1-(6-methylpyridin-3-yl)-2-[(4-(methyl-sulphonyl)phenyl]ethanone (Aqueous NaOH as Base)

41.07 g (89.1%, 1.00 eq.) of N,N-diethylamino-(6-methylpyridin-3-yl)acetonitrile, 30 ml of toluene and 10.0 g of Celite were initially charged. 72 g (5 eq.) of a 50% aqueous NaOH solution were then added over a period of 15 minutes such that the temperature could be maintained at 20° C. The reaction mixture was heated to 45° C. With vigorous stirring, a first portion of 0.32 g of tetra-n-butylammonium bromide was added. Immediately after that, a solution of 0.32 g of tetra-n-butylammonium bromide and 44.52 g (1.2 eq.) of 4-(methylsulphonyl)benzyl chloride in 200 ml of toluene was added over a period of 1.5 h. After half had been added, a third portion of 0.32 g of tetra-n-butylammonium bromide was added, and stirring was continued at 45° C. for 6 h.

The reaction mixture was then warmed to room temperature, and 100 ml of water and 100 ml of toluene were then added. The mixture was filtered, the residue was washed with 25 ml of toluene and the phases were then separated. The aqueous phase was extracted with 2×50 ml of toluene. The combined organic phases were then extracted with 380 ml of 1N HCl. Neutralization with 29.6 g of 50% aqueous NaOH solution to pH 4.5 resulted in the title product crystallizing out. The suspension was filtered and the product was washed with 2×100 ml of water and 2×80 ml of isopropanol/water 1:1 and subsequently dried at 20° C./20 mbar.

This gave 40.19 g (76.4%) of the title product having a content of 99.0%.

M.p. 182° C.-183° C.
$^1$H-NMR (CDCl$_3$) 9.15 (1H, s);
8.18 (1H, d);
7.92 (2H, d);
7.47 (2H, d);
7.30 (1H, d);
4.39 (2H, s);
3.04 (3H, s);
2.63 (3H, s).

EXAMPLE 4b

Preparation of 1-(6-methylpyridin-3-yl)-2-[(4-(methyl-sulphonyl)phenyl]ethanone (Alkoxide, Anhydrous)

At 20° C., 48.16 g (84.5%, 1.00 eq.) of N,N-diethylamino-(6-methylpyridin-3-yl)acetonitrile in 20 ml of tetrahydrofuran were added over a period of 30 minutes to a suspension of 38.58 g (1.7 eq.) of potassium t-butoxide in 60 ml of tetrahydrofuran. Immediately afterwards, 42.59 g (1.03 eq.) of 4-(methylsulphonyl)benzyl chloride in 60 ml of tetrahydrofuran were added at from 20° C. to 25° C. over a period of 1.5 h.

The reaction mixture was stirred at 20° C. for 0.5 h and then diluted with 100 ml of water, and adjusted to pH 2 by addition of 180 ml of 2N HCl over a period of one hour. After a further 0.5 h at 20° C., the mixture was adjusted to pH 3 using 10 g of a 30% aqueous NaOH solution. The suspension was stirred at 20° C. for one hour and then filtered, and the product was washed with 2×150 ml of water and 2×100 ml of water/isopropanol 1:1. Drying at 20° C./20 mbar gave 53.72 g (92%) of the title product having a content of 99.1%.

M.p. 182° C.-183° C.
$^1$H-NMR (CDCl$_3$): 9.15 (1H, s);
8.18 (1H, d);
7.92 (2H, d);
7.47 (2H, d);
7.30 (1H, d);
4.39 (2H, s);
3.04 (3H, s);
2.63 (3H, s).

The invention claimed is:

1. A process for preparing 1-(6-methylpyridin-3-yl)-2-[4-(methylsulfonyl) phenyl]ethanone of the formula:

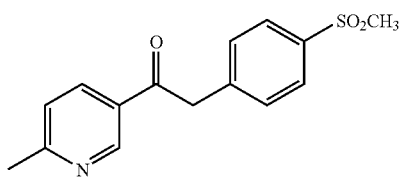

I comprising reacting N,N-dialkylamino-(6-methyl-3-pyridyl)acetonitrile of the formula:

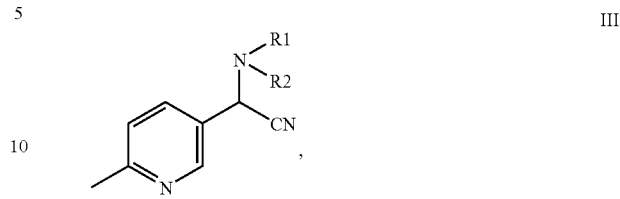

III wherein R$^1$ and R$^2$ are identical or different and are C$_{1-4}$-alkyl, in the presence of a base with a 4-(methylsulfonyl) benzyl halogenide to give 1-(6-methylpyridin-3-yl)-2-[4-(methylsulfonyl)phenyl]ethanone, wherein the base is an alkali alcoholate and is used in the presence of an organic solvent at a temperature of 15 to 25° C.

2. The process according to claim 1, wherein the 4-(methylsulfonyl)benzyl halogenide is 4-(methylsulfonyl)benzyl chloride.

3. The process according to claim 2, wherein the acetonitrile is added to a water-free suspension of the alkali alcoholate.

4. The process according to claim 3, wherein the alkali alcoholate is selected from the group consisting of sodium tert-butanolate, potassium tert-butanolate and sodium tert-pentanolate.

5. The process according to claim 4, wherein the alkali alcoholate is potassium tert-butanolate.

6. The process according to claim 5, wherein the organic solvent is an ether.

7. The process according to claim 6, wherein the ether is tetrahydrofuran.

8. The process according to claim 1, wherein the acetonitrile is added to a water-free suspension of the alkali alcoholate.

9. The process according to claim 1, wherein the alkali alcoholate is selected from the group consisting of sodium tert-butanolate, potassium tert-butanolate and sodium tert-pentanolate.

10. The process according to claim 9, wherein the alkali alcoholate is potassium tert-butanolate.

11. The process according to claim 1, wherein the organic solvent is an ether.

12. The process according to claim 11, wherein the ether is tetrahydrofuran.

* * * * *